United States Patent
Nilsson et al.

[11] Patent Number: 6,132,405
[45] Date of Patent: Oct. 17, 2000

[54] CATHETER FOR PERITONEAL DIALYSIS

[75] Inventors: Christer Nilsson, Landskrona; Joakim Oscarson, Lund; Jan-Bertil Jeppsson, Lomma, all of Sweden

[73] Assignee: Gambro AB, Sweden

[21] Appl. No.: 09/051,384

[22] PCT Filed: Oct. 9, 1996

[86] PCT No.: PCT/SE96/01280

§ 371 Date: May 6, 1998

§ 102(e) Date: May 6, 1998

[87] PCT Pub. No.: WO97/13543

PCT Pub. Date: Apr. 17, 1997

[30] Foreign Application Priority Data

Oct. 10, 1995 [SE] Sweden ................. 9503562

[51] Int. Cl.[7] .................. A61M 5/00; A61M 1/00
[52] U.S. Cl. .................. 604/264; 604/29
[58] Field of Search ............ 604/264, 29, 30, 604/102, 166, 169, 239, 266, 271, 272, 39, 35; D24/112; 138/DIG. 11

[56] References Cited

U.S. PATENT DOCUMENTS

| | | | |
|---|---|---|---|
| D. 236,920 | 9/1975 | Sheridan | D24/112 |
| 2,139,653 | 12/1938 | Belfrage | 604/39 |
| 3,386,438 | 6/1968 | Stevens | 604/264 |
| 3,674,033 | 7/1972 | Powers | 604/29 |
| 3,828,767 | 8/1974 | Spiroff | |
| 4,002,174 | 1/1977 | Reed et al. | 604/264 |
| 4,437,856 | 3/1984 | Valli | 604/29 |
| 4,769,016 | 9/1988 | Labianca | 604/280 |
| 4,863,441 | 9/1989 | Lindsay et al. | 604/264 |
| 5,057,073 | 10/1991 | Martin | |
| 5,084,033 | 1/1992 | O'Neill et al. | 604/264 |
| 5,300,022 | 4/1994 | Klapper et al. | 604/264 |
| 5,364,373 | 11/1994 | Waskoenig et al. | 604/272 |
| 5,380,307 | 1/1995 | Chee et al. | 604/264 |
| 5,484,423 | 1/1996 | Waskoenig et al. | 604/272 |
| 5,578,006 | 11/1996 | Schoen | 604/264 |
| 5,616,137 | 4/1997 | Lindsay | 604/264 |
| 5,643,226 | 7/1997 | Cosgrove et al. | 604/264 |
| 5,662,619 | 9/1997 | Zarate | 604/264 |

FOREIGN PATENT DOCUMENTS

| | | |
|---|---|---|
| 0 185 865 | 7/1986 | European Pat. Off. |
| 0 191 234 | 8/1986 | European Pat. Off. |
| 0 381 062 | 8/1990 | European Pat. Off. |
| 0 631 508 | 1/1995 | European Pat. Off. |
| 8606282 A1 | 11/1986 | WIPO |
| 8902290 A1 | 3/1989 | WIPO |

*Primary Examiner*—Sharon Kennedy
*Attorney, Agent, or Firm*—Lerner, David, Littenberg, Krumholz & Mentlik, LLP

[57] ABSTRACT

Catheters are disclosed for insertion into a body cavity. The catheters include a region near the distal end of the catheter which includes a number of apertures as well as a reduced diameter portion which has a diameter less than the diameter of the rest of the catheter region so that the flow of a fluid through the reduced diameter portion is reduced thereby.

32 Claims, 3 Drawing Sheets

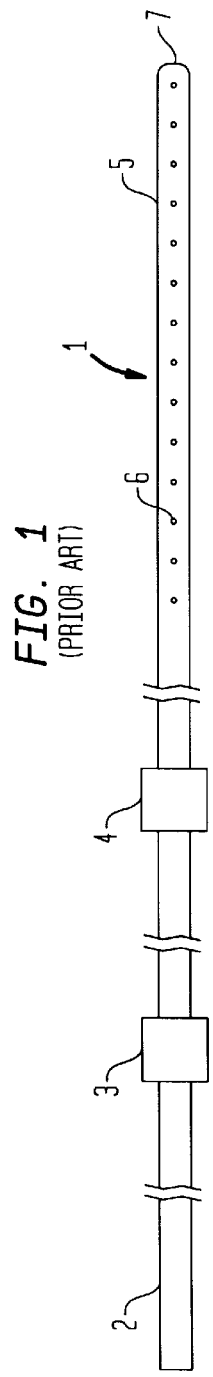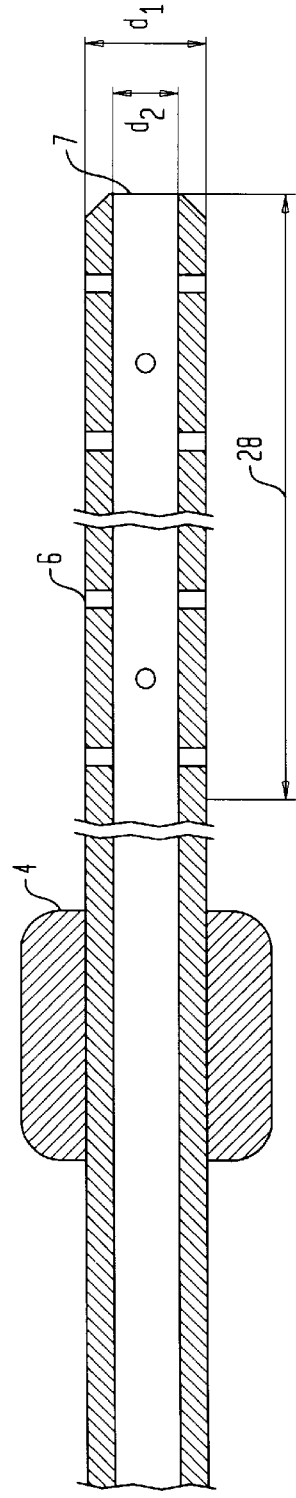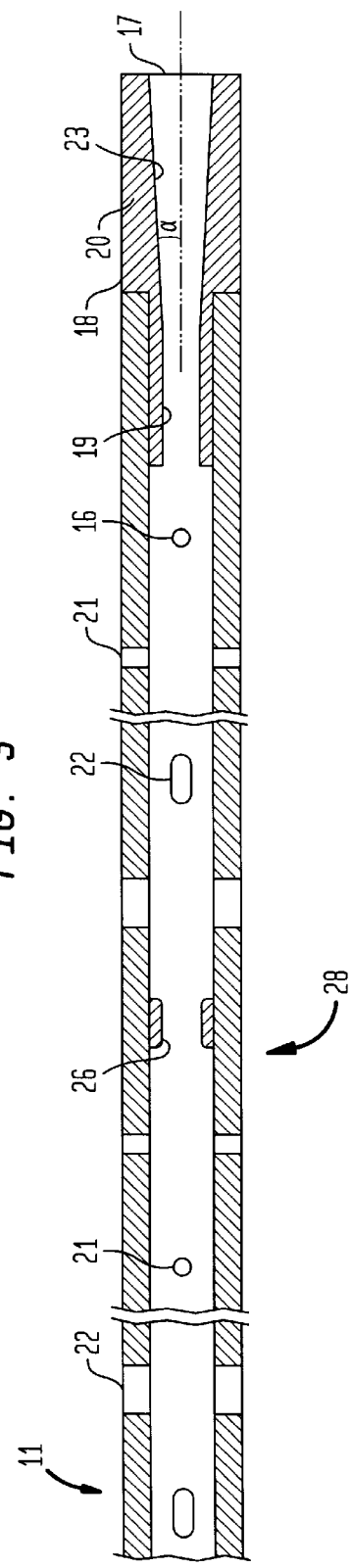

CATHETER FOR PERITONEAL DIALYSIS

FIELD OF THE INVENTION

The present invention relates to a catheter, particularly intended for use with peritoneal dialysis. In particular, the invention relates to a peritoneal dialysis catheter suitable for high flow speeds while preventing significant catheter migration. The catheter according to the invention can also be used in other circumstances, such as with the connection to other cavities or vessels in the body, like the stomach, the intestine, the urine bladder, the heart, the brain etc., as well as for connection to blood vessels.

BACKGROUND ART

With peritoneal dialysis, a catheter is used for the supply and removal of dialysis liquid to/from the peritoneal cavity.

A commonly-used catheter is the so-called Tenckhoff-catheter which can be of the straight type or the spiral-shaped type. This catheter consists of a silicon tube, on to which are fastened two dacron pads, to which peritoneal fibres may grow attached, thereby fixing the catheter in position after surgical implantation.

The proximal end of the catheter is connected by means of a connector to a dialysis liquid supply arrangement. The distal end of the catheter is provided with a plurality of holes in its sidewall and generally ends in an opening.

One problem with this catheter is that the holes in the catheter can be blocked during the outward-feed phase, due to the effect of the suction pressure. During the inward-feed phase, too high flows can lead to the catheter moving into the peritoneal cavity. The force which occurs when the fluid flows out causes the tip of the catheter to lash about and to be displaced when the flow is initiated. This catheter migration is one of the reasons for a catheter having to be changed. This movement can also affect the peritoneal membrane's susceptibility to infection.

The liquid also flows out of the catheter through the side holes and, if the flow speed in the sideways direction is too high, discomfort to the patient may result. The flow speed in the forward direction may also cause the patient discomfort.

Catheters for different purposes are described in patent literature. For example, the patent document EP-A1-185 865 relates to an implantable intraperitoneal catheter provided with several spacers in the form of discs which protect the holes in the side of the catheter from becoming blocked by ingrowth. The spacers probably also have a protective effect on the peritoneal membrane which is kept away from the holes where the out-feed flow speed is at its largest. The distal end of the catheter is normally closed but may also be open.

The patent document EP-B1-381 062 describes a catheter for even distribution of therapeutic fluids and comprises a catheter with a plurality of holes along the catheter's sidewall. The diameter of the holes increases towards the distal end of the catheter which is closed. The very small holes are manufactured by laser technology and are rectangular or oblong.

The patent document WO 89/02290 describes a catheter for placement in the ventricular system in the brain. The catheter comprises many small holes which are drilled at an angle with respect to the normal, vis-a-vis the catheter wall.

The patent document U.S. Pat. No. 5,057,073 describes a double-lumen catheter for implanting into a patient's vein, for use with hemodialysis treatments. The catheter implanted with the help of a Seldinger thread and the catheter's distal end tip opening is formed with a restriction in order to fit around the Seldinger thread. The wall of the catheter is provided with a plurality of holes for the passage of blood into, and out of, the catheter.

The patent document EP-B1-191 234 discloses a process for providing a medical tube with grooves or slits.

With a straight catheter for peritoneal dialysis having an open distal end, a large part of the total flow, as much as two-thirds, will pass out through the tip opening. High outflow speeds thereby result, which could damage the fibres in the peritoneum. Additionally, the force which acts on the tip of the catheter due to the outflow of fluid in an axial direction becomes excessively high. It is this force which causes the catheter to lash about and be displaced when the flow is initiated. It is desirable to reduce this force, particularly at higher flows.

The problem is greater for shorter catheters with fewer side holes and with straight catheters. With higher mass flows, the proportion which flows out through the tip becomes larger when viewed as a percentage. If the flow is doubled, the outflow speed through the open tip is more than twice as high and the resulting force more than quadruples.

SUMMARY OF THE INVENTION

The object of the present invention is to achieve a catheter, particularly intended for peritoneal dialysis, which can be used for higher flows and have lower flow resistance.

Another object of the present invention is to achieve a catheter wherein the force which affects the tip due to the flow out from an opening in the tip of the catheter, is minimised.

An additional object of the present invention is to achieve a catheter where the outflow through the side holes is as equal as possible.

A simple way of minimising the catheter's flow resistance is to increase its diameter. This can however give rise to medical problems, like increased susceptibility to infection or a larger risk of leakage.

In order to minimise the flow resistance with an unchanged diameter, it is possible to increase the combined area of the holes in the catheter's sidewall and tip.

As described above, a large part of the liquid flows through the catheter's tip opening, which significantly effects the patient and the catheter. By minimising the flow through the tip opening it ought to be possible to divide the out-going flow over a larger area, which would be beneficial for the patient.

According to the present invention, the distal end of the catheter is therefore provided with a restriction, so that a smaller part of the total flow passes out through the tip opening. It is preferred that less than 50% of the total flow passes out through the tip opening and it is particularly preferred that between 20% and 25% of the total flow passes out though the tip opening. A smaller tip opening is also possible so that more than 5% to 10% of the total flow passes out through this opening.

If the catheter is provided with a restriction so that the flow through the tip opening is 20% to 25% of the total flow, the speed through the opening is however still so great that the problem of the force excerted on the tip of the catheter remains. In order to further reduce this force, without restricting the flow through the tip completely, the tip can be provided with both a restriction which reduces the flow and a conic diffusor which increases the flow diameter and thereby reduces both the speed and the force of the out-going flow.

As explained above, the diffusor's main task is to reduce flow speed rather than to recover pressure. The increase of the diameter for the flow should occur gradually such that the liquid will flow smoothly along the diffusor's internal surface and therefor without relief. A suitable tip angle ($\alpha$) with respect to a longitudinal axis of the channel of the diffusor is between 3 and 30 degrees, preferably 5 to 15 degrees. Particularly preferred is about 8 to 10 degrees.

According to a preferred embodiment of the invention, the tip can be manufactured as a separate part, or tip insert, which is fixed to the otherwise tube-shaped catheter by means of welding or adhesive. The insert can be manufactured of the same material as the rest of the catheter, such as silicon or polyurethane.

According to a preferred embodiment of the invention, the insert is manufactured of a metal such as titanium or tungsten. In this way, the catheter's tip is somewhat heavier which may be an advantage in certain circumstances. Other metals may also be used if the insert is provided with a coating of a biocompatible material, i.e. the insert is cast in a plastic material. The insert may be cast in the catheter during its manufacture, which thus occurs in one single step.

In order to achieve an even distribution of the outflow through the holes in the catheter's sidewall, these holes are formed having different sizes so that the holes which are nearest to the distal end of the catheter have the smallest diameter. By forming the holes in this way, the first holes, where the flow speed is high and therefore the static pressure is low, have a flow which is the same as that in the smaller holes which are located more distal along the catheter towards the tip where the static pressure is higher and the flow speed is lower. Additionally, only a small part of the area of the first larger holes will be used for effective flow, due to the fact that the fluid in the catheter has a flow component towards the end of the catheter. In order to increase the effective area of the hole, these are, according to the present invention, formed ovally in the longitudinal direction of the catheter.

In order to reduce the flow speed out through the holes, a plurality of holes may be provided. If too many holes are provided, however, the catheter will be too soft or weak. The same occures if holes too large in diameter are used.

In accordance with a preferred embodiment of the invention, a restriction may be arranged along the catheter's length between the proximal holes and the distal holes. The restriction raises the static pressure for the proximal holes which can therefore be made smaller, while reducing the flow speed at the same time.

Holes of different size may thus be arranged along the length of the catheter so that the first holes, as seen from the proximal end, are large and oblong and thereafter diminish in size towards the restriction, while immediately after the restriction the holes may be larger again and diminish in size towards the catheter's distal end. In this way, a substantially equal outflow through all the holes is obtained.

If a restriction is introduced into the catheter, it can be expected that the catheter will have a higher total flow resistance. If, however, the restriction is placed further from the distal end, for instance two-thirds distance from the distal end calculated along the part of the catheter provided with holes, referred to as the vented catheter region, a somewhat reduced total flow resistance is obtained. It is therefore preferred that the restriction is placed at between about 50% and 80% distance from the distal end of the catheter, preferably at about 65% distance, of the vented catheter region as measured from the distal end.

Additional features, advantages and characteristics of the catheter according to the invention will be apparent from the following detailed description of preferred embodiments of the invention with reference to the drawings.

BRIEF DESCRIPTION OF THE DRAWINGS

FIG. 1 is a side view of a catheter of the type CD-5001 and depicts a typical example of a catheter according to the state of the art.

FIG. 2 is an enlarged cross-sectional view through the catheter of FIG. 1.

FIG. 3 is an enlarged cross-sectional view similar to FIG. 2, but provided with a tip insert according to the present invention.

DESCRIPTION OF PREFERRED EMBODIMENTS

Figure 4:
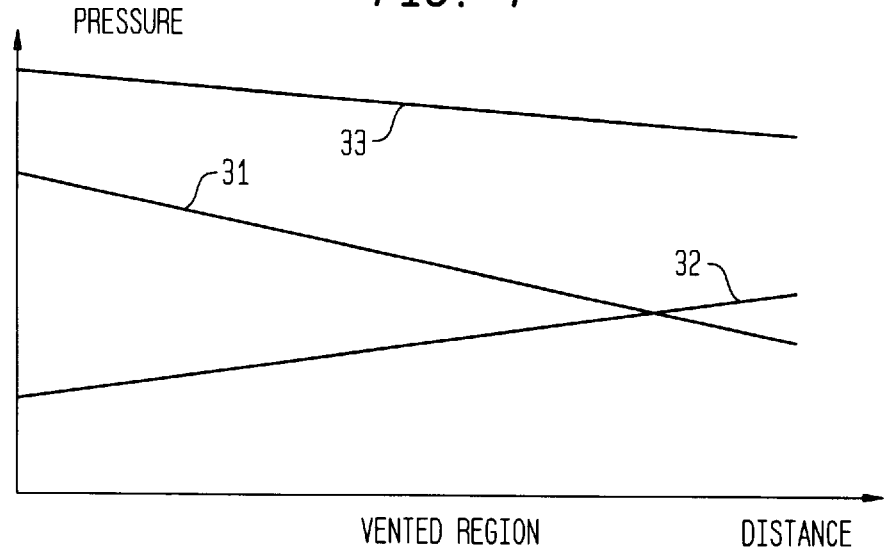
FIG. 4 is a schematic diagram of the pressure conditions inside the catheter.

FIG. 1 shows a side view of a catheter of known type. The catheter 1 consists of a flexible tube of silicon, which at its proximal end 2 is connected with an arrangement for the supply or removal of dialysis liquid, which is not shown on the drawing.

At the end 2, the catheter is provided with two dacron pads 3, 4. When the catheter is surgically implanted in the peritoneal cavity, the two pads 3 and 4 are at such positions in the insertion tunnel that peritneal fibres may grow attached to the pads 3, 4 and fix the position of the catheter, and thereby prevent infection through the insertion tunnel. The proximal end 2 of the catheter is located outside the skin.

The distal end 5 of the catheter is located inside the peritoneal cavity and is provided with a plurality of holes 6 along its sidewall and a tip opening 7. The catheter is shown in enlarged cross-section in FIG. 2.

In this embodiment, the outer diameter of the catheter $d_1$ is 5.0 mm and the inner diameter $d_2$ is 2.7 mm. There may be fifty-six holes with a respective spacing of 3.2 mm and with a hole diameter of about 0.7 mm positioned along the vented catheter region, which may have a length of 90 mm. The holes are approximately equal in size. These specifications may, however, vary considerably between different catheters and each manufacturer has its own constructions and preferences.

FIG. 3 shows a catheter according to a preferred embodiment of the present invention. The catheter 11 is provided with a plurality of holes 16 along the wall of the catheter defining the vented catheter region 28.

The catheter may comprise an insert 18, which further comprises a restriction 19, as well as an enlarging portion 20, for example in the form of a diffusor with even cross-sectional enlargement 23 (conical) and concludes in a tip opening 17. The inner diameter of the restriction may be 1.5 mm and the diffusor's conicity may be about 8° which, with a length of about 9 mm, results in a final opening diameter of about 2.7 mm, i.e. the same as the original inner diameter of the catheter.

The insert 18 can preferably be dimensioned so that the flow speed through the tip opening is approximately the same as the flow speed through the holes in the catheter's sidewall (see below for more detail).

With the aforementioned dimensions the flow through the tip opening is about 20% of the flow through the side holes, which has shown itself to be a suitable value. By means of this dimensioning, the advantage is obtained that the force which the flow exerts on the catheter tip is not too large and does not cause the catheter to move to too large a degree, i.e. catheter migration is avoided. Additionally, the flow speed through the tip opening is relatively slow, whereby the effect on the peritoneal cavity is minimised.

With certain types of catheter, it is suitable if the flow through the tip opening is less than that which is stated above, for example more than 5 or 10% of the total flow. This is true particularly for catheters with many holes in the sidewall. In certain cases, it can also be favourable if the tip opening is not present.

In other cases it may be better if a larger part of the total flow passes through the tip opening, such as up to 50% or more of the total flow. Normally however, it is preferred that about 20% to 25% of the total flow passes through the tip opening.

The insert 18 is preferably manufactured of the same material as the rest of the catheter, such as silicon. The whole catheter is preferably made in one single piece in the same manufacturing step. Alternatively, the insert 18 can be manufactured by itself in the same material, or in another material, and be fastened to the catheter tip by means of welding or adhesive, which is of course done in a biocompatible manner.

Alternatively, the insert can be manufactured of a biocompatible plastic material such as polyurethane or polycarbonate.

In a further alternative embodiment of the invention, the insert is made of metal such as titanium or tungsten and thereby has a somewhat larger weight than if it was made of plastics material. This is favourable since the tip of the catheter will thereby automatically be orientated downwardly in the peritoneal cavity, which is generally preferred.

The insert can be embedded in a plastic material which is biocompatible. Other metals can also be used such as silver which also has a certain bacteriostatic function.

In the preferred embodiment of the invention as shown in FIG. 3, the holes 16 are depicted as having different sizes. The object of using holes with different sizes is to obtain approximately the same flow speed out through the various holes.

FIG. 4 shows a schematic diagram of the pressure conditions within the vented catheter region as the liquid moves toward the catheter tip. The pressure in the catheter is made up of a dynamic pressure which corresponds to the movement energy of the fluid (see curve 31) and a static pressure which constitutes the fluid's pressure against the catheter wall (see curve 32). The sum of the dynamic pressure and the static pressure corresponds to the total pressure (see curve 33). For the sake of simplicity, no account is taken of the hydrostatic pressure.

As shown by curve 31, the dynamic pressure drops towards the catheter tip which is dependent on the fact that the fluid's flow speed is reduced due to what is given out through the side holes. At the same time, the static pressure rises as shown by curve 32. The total pressure reduces slightly due to, inter alia, the frictional effect against the catheter's sidewall.

The static pressure at each side hole 16 determines the flow speed through that hole. Thus, the side holes must have a lesser diameter nearer to the tip in order for the same flow speed to be obtained from all the holes, whereby the frictional losses against the sidewall of the hole as well as the losses due to the fluid's viscosity reduce the outflow speed. A reduction in the outflow speed can probably be obtained alternatively with conical holes where the diameter increases outwardly. Such holes can be manufactured with laser technology or in another way, such as by conical stamps.

In practice, the diameter of the holes does not have to be adapted accurately to the static pressure and it is normally sufficient if two or three different diameters are used. In FIG. 3, the holes 21 are shown with a small diameter close to the catheter tip and holes 22 with a larger diameter further away from the catheter's tip.

Figure 5:
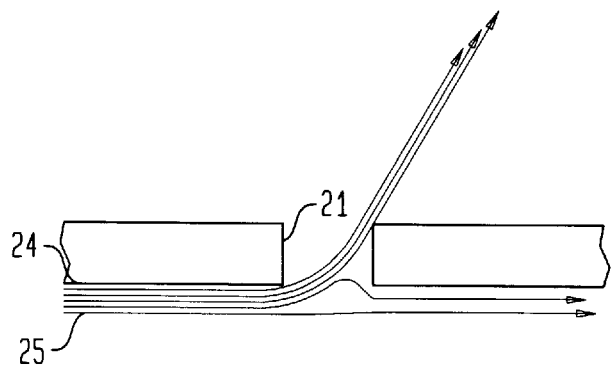
FIG. 5 is a schematic flow diagram at a side hole in the catheter.

FIG. 5 schematically shows the flow picture for a circular, relatively small hole 21 in the catheter's sidewall. Along the flow lines 24 which lie closest to the sidewall, the fluid particles have a relatively low speed and can therefore, without any great difficulty, be diverted outwardly by the static pressure and pass out through the hole 21. Along the flow lines 25 which are further from the sidewall, the fluid particles are however more difficult to divert and do not manage to be adequately diverted before the hole 21 has been passed. The effective surface area of the hole 21 is therefore reduced. The effective surface area is dependent on the flow speed of the fluid at the hole. In order to obtain the same effective surface area, the hole's cross-sectional area therefore has to be increased further from the catheter tip.

There are thus two reasons for increasing the hole diameter further away from the catheter's tip. It is, however, not possible to increase the hole's diameter too much as the catheter becomes too weak and flexible.

Therefore, in accordance with the present invention, it is proposed to use oblong holes 22, such as are clearly shown in FIG. 3, for the holes which require a larger cross-sectional area. The advantage is thereby obtained that the effective surface area of the hole is used better than with completely circular holes. Additionally, oblong holes affect the integrity of the catheter less so that it does not become too flexible.

It can be difficult to manufacture holes with sufficiently large surface area, despite the measures which are indicated above. It is therefore proposed in accordance with the present invention, that a restriction 26 is arranged approximately in the middle of the vented catheter's region which is provided with holes, as shown in FIG. 3. However, the use of this restriction 26 is optional.

Figure 8:
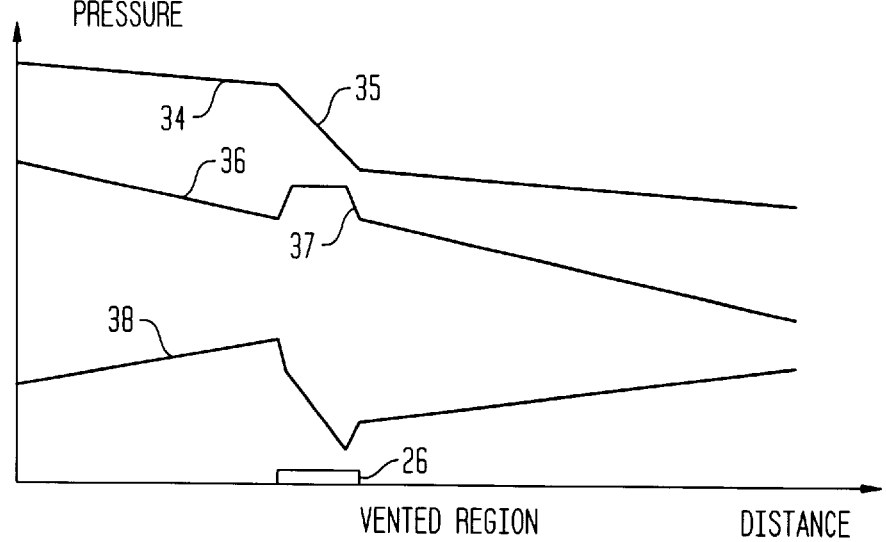
FIG. 8 is a schematic diagram similar to FIG. 4, of the pressure conditions in a catheter provided with a restriction.

As shown schematically in FIG. 8, the restriction achieves a reduction 35 of the total pressure due to the frictional forces along, and the energy losses across, the restriction, which means that the static pressure is reduced over the restriction since the dynamic pressure is unchanged before and after the restriction (the same flow speed). The static pressure before the restriction is also somewhat higher than without the restriction.

It is therefore possible to use oblong holes 22 furthest away from the tip, followed by small circular holes 21 nearer to the tip and towards the restriction 26. After the restriction oblong holes 22 are first used again and then small circular holes 21 closest to the tip. In this way, approximately the same flow speed is obtained through the various holes.

It can be expected that the total flow resistance for a catheter with such a restriction 26 would be greater than without a restriction. However, it has discovered that, if the restriction is placed in a certain way, the total flow resistance of the catheter may be minimised. If the restriction is placed about two thirds distance from the tip along the portion of the catheter provided with holes, about the same or even a lower flow resistance is obtained compared to when no restriction is present. According to the invention, a restriction is arranged at a distance of between 50%–80% of the length of the vented catheter region, as measured from the tip. An explanation of this unexpected result may be that the holes before the restriction are used more effectively due to the increased static pressure in this portion.

In a preferred embodiment of the invention forty-eight holes are used, divided in the following way seen from the catheter's tip. First there are ten circular holes with a diameter of 0.8 mm, followed by eighteen oblong holes with the dimensions 0.9 mm×2.0 mm. Then there is a restriction, followed thereafter by ten small circular holes with a diameter of 0.8 mm, followed by 10 oblong holes having the dimensions 0.9 mm×2.0 mm. The distance between the holes is 5 mm.

The restriction is dimensioned so that the flow speed through the various holes is as similar as possible. A suitable dimension is an inner diameter of 2.0 mm with a length of about 4 mm. The size is also dependent on how the inner surface of the restriction looks and on the geometry of the restriction. If the surface is rough or edged, the restriction can be shortened.

Figure 6:
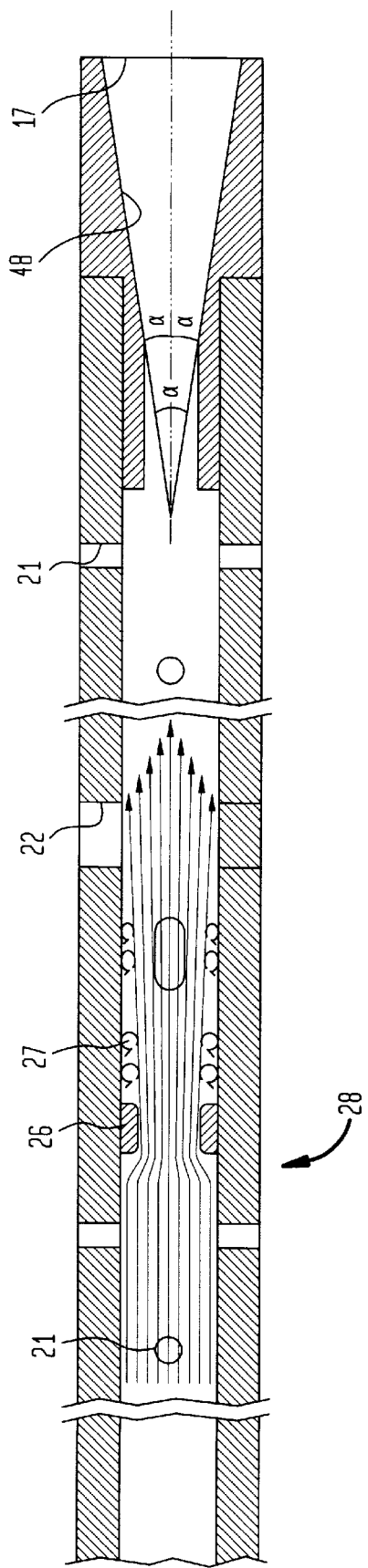
FIG. 6 is a cross-sectional view similar to FIG. 3, schematically showing the flow at a restriction in the part of the catheter provided with holes.

As shown in more detail in FIG. 6, the restriction 26 induces eddies 27 in the fluid flow after the restriction. These eddies cause a loss of energy which reduces the total pressure and thus also the static pressure. Moreover, energy losses arise due to frictional forces against the wall of the restriction (increased flow speed) and due to the viscosity.

The pressure conditions before and after the restriction 26 are shown schematically in FIG. 8. The curve 34 for the total pressure shows a steep drop 35 at the restriction. The curve for the dynamic pressure 36 rises sharply at the restriction as shown by a hump 37, but returns thereafter to the same value as before the restriction, since the flow speeds are the same. The curve 38 gives the static pressure, which rises before the restriction but sinks to a lower value after the restriction, approximately corresponding to the starting value, and then rises. The two curve portions of the static pressure before and after the restriction are about the same. In this manner the two parts of the portion provided with holes are used in approximately the same way.

The aforementioned features can be combined in different ways to give the catheter desired characteristics. With catheters which are to be used for extra-sensitive patients, it may be possible to use a long portion provided with holes, which portion has many holes, and thereby use more than one restriction, such as two or three along the length of the portion having holes.

Figure 7:
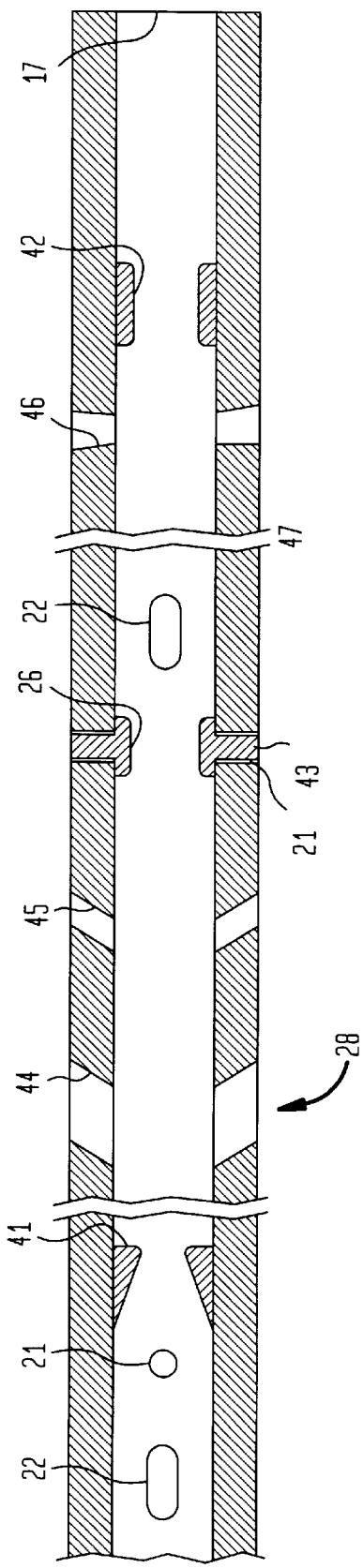
FIG. 7 is a cross-sectional view similar to FIG. 3, of one alternative embodiment of the invention.

Referring to FIG. 7 it may be possible to replace the insert 18 with a restriction 42 which is relatively close to the catheter tip, but also sufficiently removed from the tip opening 17 in order that the jet which is obtained from the restriction will have collected into a homogeneous flow.

The restriction 42 is positioned about 20 mm from the tip opening 17, allowing the flow to collect and reduce in speed before the flow passes through the tip opening 17.

The restrictions 26 and 42 are preferably manufactured of the same material as the rest of the catheter, such as of silicon. The whole catheter is preferably produced in one single piece and in the same manufacturing step. Alternatively, the restrictions may be inserts which are introduced into the catheter and fixed in a suitable way such as by welding or adhesive. Alternatively, the restriction 26 can be mechanically fixed by being provided with projecting pins 43 which fit into holes 21 in the catheter's sidewall. The same materials can be used as for the insert (see above).

The length of, or the tip angle of, the conical portion 20 can be increased so that the orifice has a larger cross-section than the rest of the catheter. FIG. 6 shows an insert 48 with larger tip angle which results in a larger outlet area and lower outflow speed.

FIG. 7 shows further alternative embodiments of the restrictions and holes. A conical restriction 41 is thus shown which consists of a conically diminishing portion, followed by a relatively sharp edge. The fluid's flow speed increases in the conical portion, which results in a large eddy formation after the sharp edge. This eddy formation brings about energy losses which result in a drop of the total pressure and the static pressure. Additionally, energy losses arise in the form of friction losses against the walls as well as internally in the fluid due to the viscosity.

In order to avoid the effect which is shown in FIG. 5, where only a part of the hole's effective surface area is used, it is proposed that the holes 44 and 45 are arranged at a small angle relative to the normal to the sidewall, such as 10°. Such a slanted arrangement is most noticeable at the start of the portion provided with holes where the flow speed is at its largest.

It can be difficult to reduce the static pressure sufficiently, close to the tip of the catheter. Thus, the small holes at this end can be slightly conically widened, as shown by the hole 46. Since the wall thickness is relatively small, the speed reduction will of course be correspondingly small. This hole can also be arranged in a slanted manner as shown by the hole 47.

The flow conditions for flow of fluid into the peritoneal cavity have been described above. With outward flow, an underpressure is used which sucks the fluid out of the peritoneal cavity. For this, the proximal holes furthest from the tip are used mainly. The fluid passes to a very small extent through the tip opening and the distal holes as well as past the restriction. Only when the proximal holes become blocked due to the fluid at these holes being used up and the catheter sucking on to the peritoneal membrane, does flow occur through the distal holes. This has the beneficial effect that the restrictions do not become blocked by fibres or larger particles which may be present in the fluid in the peritoneal cavity.

The invention has been described above with reference to the embodiments shown in the drawings. The various components and characteristics can however be combined in different ways than have been shown in the drawings and other combinations are included within the scope of the invention. The invention is only limited by the appended claims.

What is claimed is:

1. A catheter adapted for insertion into a body cavity, said catheter including a proximal end, a distal end for insertion into said body cavity, and an inner flow channel, said catheter including a vented catheter region proximate to said distal end of said catheter and having a substantially constant internal diameter including a first internal diameters, a plurality of apertures, a restriction portion arranged in said vented catheter region and having a diameter less than said internal diameter, and an enlarging portion disposed between said restriction portion and said distal end of said catheter, said enlarging portion providing an expanded diameter inner flow channel, at least a portion of which having an inner diameter greater than said first internal diameter.

2. The catheter of claim 1, wherein said distal end of said catheter comprises a catheter tip including a tip opening.

3. The catheter of claim 2, wherein said portion of said catheter between said restriction portion and said tip opening is free of any of said plurality of apertures.

4. The catheter of claim 2, wherein said vented catheter region having said first internal diameter is adapted to provide for a predetermined total fluid flow therethrough, and said restriction portion and said enlarging portion are dimensioned such that the flow of said fluid through said tip opening provides between about 5% and 50% of said predetermined total fluid flow.

5. The catheter of claim 4, wherein said flow of said fluid through said tip opening comprises between about 20% and 25% of said predetermined total fluid flow.

6. The catheter of claim 2, wherein said plurality of apertures and said tip opening are dimensioned such that the rate of flow of a fluid through said plurality of apertures and through said tip opening are substantially equal.

7. The catheter of claim 2, wherein said plurality of apertures includes at least one first aperture adjacent said tip opening having a first cross-sectional area and at least one second aperture further away from said tip opening having a second cross-sectional area, said first cross-sectional area being less than said second cross-sectional area.

8. The catheter of claim 7, wherein said catheter has a longitudinal axis, and wherein said cross-sectional area of said at least one second aperture has an oval cross-section, with said longitudinal axis of said oval being substantially parallel to said longitudinal axis of said catheter.

9. The catheter of claim 1, wherein said restriction portion comprises a first restriction portion, and including a second restriction portion displaced from said first restriction portion towards said proximal end of said catheter.

10. The catheter of claim 9, wherein said portion of said catheter between said first and second restriction portions includes said plurality of apertures, and wherein the cross-sectional area of said plurality of apertures increases in the direction from said first restriction portion to said second restriction portion.

11. The catheter of claim 1, wherein said restriction portion comprises a first restriction portion, and including a second restriction portion displaced from said first restriction portion towards said proximal end of said catheter.

12. The catheter of claim 11, wherein said portion of said catheter between said first and second restriction portions includes said plurality of apertures, and wherein the cross-sectional area of said plurality of apertures increases in the direction from said first restriction portion to said second restriction portion.

13. The catheter of claim 12, wherein said enlarging portion has a diameter greater than the diameter of said restriction portion.

14. A catheter adapted for insertion into a body cavity, said catheter including a proximal end, a distal end for insertion into said body cavity, and an inner flow channel, said catheter including a vented catheter region proximate to said distal end of said catheter and having a substantially constant internal diameter including a first internal diameter, a plurality of apertures, a restriction portion arranged in said vented catheter region and having a diameter less than said internal diameter, and an enlarging portion disposed between said restriction portion and said distal end of said catheter, said enlarging portion comprising a diffuser portion comprising an expanded diameter inner flow channel with a conical configuration providing an inner flow channel with a diameter greater than said diameter of said restriction portion and having a uniformly increasing diameter in the direction towards said distal end of said catheter.

15. The catheter of claim 14, wherein said enlarging portion has a diameter which successively increases in the direction towards said distal end, beginning with a diameter substantially equal to said first internal diameter.

16. The catheter of claim 14, wherein said distal end of said catheter comprises a catheter tip including a tip opening.

17. The catheter of claim 16 wherein said portion of said catheter between said restriction portion and said tip opening is free of any of said plurality of apertures.

18. The catheter of claim 16, wherein said vented catheter region having said first internal diameter is adapted to provide for a predetermined total fluid flow therethrough, and said restriction portion and said enlarging portion are dimensioned such that the flow of said fluid through said tip opening provides between about 5% and 50% of said predetermined total fluid flow.

19. The catheter of claim 18 wherein said flow of said fluid through said tip opening comprises between about 20% and 25% of said predetermined total fluid flow.

20. The catheter of claim 14 wherein said conical configuration of said inner flow channel comprises an inner wall surface having an angle with respect to a longitudinal axis of said channel of between about 1° and 10°.

21. The catheter of claim 20 wherein said inner wall surface has an angle with respect to a longitudinal axis of said channel of between about 2° and 8°.

22. The catheter of claim 21 wherein said inner wall surface has an angle with respect to a longitudinal axis of said channel of between about 4° and 5°.

23. The catheter of claim 16 wherein said plurality of apertures and said tip opening are dimensioned such that the rate of flow of a fluid through said plurality of apertures and through said tip opening are substantially equal.

24. The catheter of claim 16, wherein said plurality of apertures includes at least one first aperture adjacent said tip opening having a first cross-sectional area and at least one second aperture further away from said tip opening having a second cross-sectional area, said first cross-sectional area being less than said second cross-sectional area.

25. The catheter of claim 24 wherein said catheter has a longitudinal axis, and wherein said cross-sectional area of said at least one second aperture has an oval cross-section, with said longitudinal axis of said oval being substantially parallel to said longitudinal axis of said catheter.

26. The catheter of claim 14, wherein said restriction portion comprises a first restriction portion, and including a second restriction portion displaced from said first restriction portion towards said proximal end of said catheter.

27. The catheter of claim 26 wherein said portion of said catheter between said first and second restriction portions includes said plurality of apertures, and wherein the cross-sectional area of said plurality of apertures increases in the direction from said first restriction portion to said second restriction portion.

28. The catheter of claim 14, wherein said diameter of said enlarging portion is greater than said first internal diameter.

29. The catheter of claim 14, further including a second restriction portion arranged between the distal end and the last hole of the vented catheter region and including an enlarging portion disposed between said restriction portion and said distal end of said catheter, said enlarging portion providing an expanded diameter inner flow channel with a diameter greater than the diameter of said restriction portion.

30. The catheter of claim 29, wherein said second restriction portion is arranged at a distance of between 50% and 80% of the length of the vented catheter region as measured from the distal end.

31. The catheter of claim 29, wherein the reduced diameter portion is placed about two thirds of the distance from the distal end along the vented catheter region.

32. The catheter of claim 29, wherein several holes are arranged on each side of said restriction portion.

* * * * *

UNITED STATES PATENT AND TRADEMARK OFFICE
CERTIFICATE OF CORRECTION

PATENT NO.    : 6,132,405
DATED         : October 17, 2000
INVENTOR(S)   : Nilsson et al.

It is certified that error appears in the above-identified patent and that said Letters Patent is hereby corrected as shown below:

Delete the specification and substitute the attached specification.
Delete the abstract and substitute the attached abstract.

Signed and Sealed this

Eighth Day of October, 2002

Attest:

Attesting Officer

JAMES E. ROGAN
*Director of the United States Patent and Trademark Office*

ABSTRACT OF THE DISCLOSURE

5      Catheters are disclosed for insertion into a body cavity. The catheters include a region near the distal end of the catheter which includes a number of apertures as well as a reduced diameter portion which has a diameter less than the diameter of the rest of the catheter region so that the flow of a fluid through the reduced diameter portion is reduced thereby.

CATHETER FOR PERITONEAL DIALYSIS

FIELD OF THE INVENTION

The present invention relates to a catheter, particularly intended for use with peritoneal dialysis. In particular, the present invention relates to a peritoneal dialysis catheter suitable for high flow speeds while preventing significant catheter migration. More particularly, the present invention relates to a catheter which can also be used in other circumstances, such as with the connection to other cavities or vessels in the body, such as the stomach, the intestine, the bladder, the heart, the brain, etc., as well as for connection to blood vessels.

BACKGROUND OF THE INVENTION

In connectin with peritoneal dialysis, a catheter is generally used for the supply and removal of dialysis liquid to and from the peritoneal cavity.

A commonly-used catheter for such purposes is the so-called Tenckhoff-catheter which can be straight or spiral-shaped. This catheter consists of a silicon tube, onto which are fastened two dacron pads, to which peritoneal fibers may grow attached, thereby fixing the catheter in position after surgical implantation.

The proximal end of such catheters are connected by means of a connector to a dialysis liquid supply arrangement. The distal end of the catheter is provided with a plurality of holes in its sidewall, and generally ends in an opening.

One problem with this type of catheter is that the holes in the catheter can be blocked during the outward-feed phase, due to the effect of suction pressure. During the inward-feed phase, too high a flow can lead to the catheter moving into the peritoneal cavity. The force which is thus created when the fluid flows out of the catheter causes the tip of the catheter to lash about and to be displaced when the flow is initiated. This catheter migration is one of the reasons for a catheter having to be changed. This movement can also affect the peritoneal membrane's susceptibility to infection.

The liquid also flows out of the catheter through the side holes and, if the rate of flow in the sideways direction is too high, discomfort to the patient may result. The rate of flow in the forward direction may also cause the patient discomfort.

Catheters for different purposes are described in the patent literature. For example, European Patent No. 185,865 relates to an implantable intraperitoneal catheter provided with several spacers in the form of discs which protect the holes in the side of the catheter from becoming blocked by ingrowth. The spacers probably also have a protective effect on the peritoneal membrane, which is kept away from these holes in which the rate of flow is at its largest. The distal end of the catheter is normally closed, but may also be open.

European Patent No. 381,062 describes a catheter for the even distribution of therapeutic fluids, and comprises a catheter with a plurality of holes along the catheter's sidewall. The diameter of the holes increases towards the distal end of the catheter, which is closed. The very small holes are manufactured by laser technology, and are rectangular or oblong.

International Patent No. WO 89/02290 describes a catheter for placement in the ventricular system in the brain. The catheter comprises many small holes which are drilled at an angle with respect to the normal, vis-a-vis the catheter wall.

U.S. Pat. No. 5,057,073 describes a double-lumen catheter for implanting into a patient's vein, for use in connection with hemodialysis treatments. The catheter implanted with the help of a Seldinger thread and the catheter's distal end tip opening is formed with a restriction in order to fit around the Seldinger thread. The wall of the catheter is provided with a plurality of holes for the passage of blood into, and out of, the catheter.

European Patent No. 191,234 discloses a process for providing a medical tube with grooves or slits.

With a straight catheter for peritoneal dialysis having an open distal end, a large part of the total flow, and as much as two-thirds thereof, will pass out through the tip opening. High outflow speeds thereby result, which could damage the fibers in the peritoneum. Additionally, the force which acts on the tip of the catheter due to the outflow of fluid in an axial direction becomes excessively high. It is this force which causes the catheter to lash about and be displaced when the flow is initiated. It is desirable to reduce this force, particularly at higher flow rates.

The problem is even greater for shorter catheters, with fewer side holes, and with straight catheters. With higher mass flows, the proportion which flows out through the tip becomes larger on a percentage basis. If the flow is doubled, the rate of outflow through the open tip is more than twice as high, and the resulting force more than quadruples.

SUMMARY OF THE INVENTION

The object of the present invention is to achieve a catheter, particularly intended for peritoneal dialysis, which can be used for higher flows and have lower flow resistance.

Another object of the present invention is to achieve a catheter wherein the force which affects the tip due to the rate of flow out of an opening in the tip of the catheter, is minimised.

An additional object of the present invention is to achieve a catheter where the outflow through the side holes is equalized as much as possible.

A simple way of minimising the catheter's flow resistance is to increase its diameter. This can, however, give rise to medical problems, like increased susceptibility to infection or a larger risk of leakage.

In order to minimise the flow resistance with an unchanged diameter, it is possible to increase the combined area of the holes in the catheter's sidewall and tip.

As described above, a large part of the liquid flows through the catheter's tip opening, which significantly effects the patient and the catheter. By minimising the flow through the tip opening it ought to be possible to divide the out-going flow over a larger area, which would be beneficial for the patient.

In accordance with the present invention, these and other objects have now been realised by the invention of a catheter which is adapted for insertion into a body cavity, the catheter including a proximal end, a distal end for insertion into the body cavity, and an inner flow channel having a predetermined diameter, the catheter including a vented catheter region proximate to the distal end of the catheter, the vented catheter region including a vented catheter region portion having the predetermined diameter and including a plurality of apertures and a reduced diameter portion providing a reduced diameter inner flow channel with a diameter less than the predetermined diameter whereby the flow of a fluid through the reduced diameter portion is reduced thereby.

In accordance with one embodiment to the catheter of the present invention, the catheter includes an expanded diameter portion disposed between the reduced diameter portion and the distal end of the catheter, the expanded diameter portion providing an expanded diameter inner flow channel with a diameter greater than the diameter of the reduced diameter portion. In a preferred embodiment, the expanded diameter portion comprises a diffuser portion comprising an inner flow channel with conical configuration providing an inner flow channel having a uniformly increasing diameter in a direction towards the distal end of the catheter.

In accordance with another embodiment of the catheter of the present invention the predetermined diameter comprises a substantially constant inner diameter, and the expanded diameter portion has a diameter substantially equal to the predetermined diameter.

In accordance with another embodiment of the catheter of the present invention, the distal end of the catheter comprises a catheter tip including a tip opening. In a preferred embodiment, the catheter includes an expanded diameter portion disposed between the reduced diameter portion and the tip opening, the expanded diameter portion providing an expanded diameter inner flow channel with a diameter greater than the diameter of the reduced diameter portion. In another embodiment, the portion of the catheter between the reduced diameter portion and the tip opening is free of any of the plurality of apertures.

In accordance with another embodiment of the catheter of the present invention, the vented catheter region having the predetermined diameter is adapted to provide for a predetermined total fluid flow therethrough, and the reduced diameter portion and the expanded diameter portion are dimensioned such that the flow of the fluid through the tip opening provides between about 5% and 50% of the predetermined total fluid flow. In a preferred embodiment, the flow of the fluid through the tip opening comprises between about 20% and 25% of the predetermined total fluid flow.

In accordance with another embodiment of the catheter of the present invention, the conical configuration of the inner flow channel comprises an inner wall surface having an angle of between about 3° and 20°, and in a preferred embodiment between about 5° and 15°, and in a more preferred embodiment between about 8° and 10°.

In accordance with another embodiment of the catheter of the present invention, the plurality of apertures and the tip opening are dimensioned such that the rate of flow of fluid through the plurality of apertures and through the tip opening are substantially equal.

In accordance with another embodiment of the catheter of the present invention, the plurality of apertures includes at least one first aperture proximate to the tip opening having a first cross-sectional area and at least one second aperture distal from the tip opening having a second cross-sectional area, the first cross-sectional area being less than the second cross-sectional area. In a preferred embodiment, the catheter has a longitudinal axis, and the cross-sectional area of the at least one second aperture has an oval cross-section, with the longitudinal axis of the oval being substantially parallel to the longitudinal axis of the catheter.

In accordance with another embodiment of the catheter of the present invention, the reduced diameter portion comprises a first reduced diameter portion, and the catheter includes a second reduced diameter portion displaced from the first reduced diameter portion towards the proximal end of the catheter. In accordance with a preferred embodiment, the portion of the catheter between the first and second reduced diameter portions includes a plurality of apertures, and the cross-sectional area of the plurality of apertures increases in the direction from the first reduced diameter portion to the second reduced diameter portion.

In accordance with another embodiment of the catheter of the present invention, the diameter of the expanded diameter portion is greater than the predetermined diameter.

In accordance with another embodiment of the catheter of the present invention, the diameter of the expanded diameter portion is substantially equal to the predetermined diameter.

According to the present invention, the distal end of the catheter is therefore provided with a restriction, whereby a smaller portion of the total flow passes out through the tip opening. It is preferred that less than about 50% of the total flow passes out through the tip opening, and it is particularly preferred that between about 20% and 25% of the total flow passes out though the tip opening. A smaller tip opening is also possible, so that more than about 5% to 10% of the total flow passes out through this opening.

The catheter can be provided with a restriction so that the rate of flow through the tip opening is about 20% to 25% of the total flow. However, the rate of flow through the opening is still so great that the problem of the force excerted on the tip of the catheter remains. In order to further reduce this force, without completely restricting the flow through the tip, the tip can be provided with both a restriction which reduces the flow and a conical diffusor which increases the flow diameter and thereby reduces both the rate of flow and the force of that out-going flow.

As explained above, the diffusor main task is to reduce the rate of flow rather than to recover pressure. The increase of the diameter for the flow should thus occur gradually, such that the liquid will flow smoothly along the diffusor's internal surface and therefor without relief. A suitable tip angle ($\alpha$) of the diffusor is between about 3 and 30 degrees, preferably about 5 to 15 degrees. Particularly preferred is about 8 to 10 degrees.

According to a preferred embodiment of the present invention, the tip can be manufactured as a separate part, or as a tip insert, which is fixed to the otherwise tube-shaped catheter by means of welding or an adhesive. The insert can be manufactured of the same material as the rest of the catheter, such as silicon or polyurethane.

According to a preferred embodiment of the present invention, the insert is manufactured of a metal such as titanium or tungsten. In this way, the catheter tip is somewhat heavier which may be an advantage in certain circumstances. Other metals may also be used if the insert is provided with a coating of a biocompatible material, i.e. if the insert is cast in a plastic material. The insert may be cast in the catheter during its manufacture, which thus occurs in one single step.

In order to achieve an ever distribution of the outflow through the holes in the catheter's sidewall, these holes are formed having different sizes so that the holes which are nearest to the distal end of the catheter have the smallest diameter. By forming the holes in this way, the first holes, where the rate of flow is high and therefore the static pressure is low, have a flow rate which is the same as that in the smaller holes which are located more distal along the catheter towards the tip, where the static pressure is higher and the flow speed is lower. Additionally, only a small portion of the area of the first larger holes will be used for effective flow, due to the fact that the fluid in the catheter has a flow component towards the end of the catheter. In order to increase the effective area of the hole, according to the present invention, these are formed ovally in the longitudinal direction of the catheter.

In order to reduce the rate of flow out through the holes, a plurality of holes may-be provided. If too many holes are provided, however, the catheter will be too soft or weak. The same occures if holes which have too large a diameter are used.

In accordance with a preferred embodiment of the present invention, a restriction may be arranged along the catheter's length between the proximal holes and the distal holes. This restriction raises the static pressure for the proximal holes which can therefore be made smaller, while reducing the rate of flow at the same time.

Holes of different sizes may thus be arranged along the length of the catheter so that the first holes, as seen from the proximal end, are large and oblong and thereafter diminish in size towards the restriction, while immediately after the restriction the holes may be larger again, and thus diminish in size towards the catheter's distal end. In this way, a substantially equal outflow through all the holes is obtained.

If a restriction is introduced into the catheter, it can be expected that the catheter will have a higher total flow resistance. If, however, the restriction is placed further from the distal end, for instance two-thirds of the distance from the distal end calculated along the part of the catheter provided with holes, referred to as the vented catheter region, a somewhat reduced total flow resistance is obtained. It is therefore preferred that the restriction is placed at between about 50% and 80% of the distance from the distal end of the catheter, preferably at about 65% of the distance, of the vented cahteter region as measured from the distal end.

BRIEF DESCRIPTION OF THE DRAWINGS

FIG. 1 is a side, elevational view of a catheter of the type CD-5001 as a representative example of a catheter according to the prior art;

FIG. 2 is an enlarged side, elevational, cross-sectional view through the catheter shown in FIG. 1;

FIG. 3 is an enlarged side, elevational, cross-sectional view of a catheter provided with a tip insert according to the present invention;

FIG. 4 is a diagramatic representation of the pressure conditions inside the catheter of the present invention;

FIG. 5 is a schematic flow diagram of a portion of a side wall hole in a catheter of the present 30 invention;

FIG. 6 is a side, elevational, cross-sectional view of a portion of a catheter in accordance with the present invention schematically showing the flow at a restriction in the portion of the catheter provided with holes;

FIG. 7 is a side, elevational, cross-sectional view of a portion of an alternative embodiment of the catheter of the present invention; and FIG. 8 is a diagramatic representation of the pressure conditions in a catheter according to the present invention provided with a restriction.

DETAILED DESCRIPTION

Referring to the Figures, in which like reference numerals refer to like elements thereof, FIG. 1 shows a side view of a catheter of a known type. The catheter 1 consists of a flexible tube of silicon, which at its proximal end 2 is connected to an arrangement for the supply or removal of dialysis liquid, which is not shown in the drawing.

At its end 2, the catheter is provided with two dacron pads, 3 and 4. When the catheter is surgically implanted in the peritoneal cavity, the two pads, 3 and 4, are at such positions in the insertion tunnel that peritoneal fibers may grow attached to the pads, 3 and 4, and fix the position of the catheter, and thereby prevent infection through the insertion tunnel. The proximal end 2 of the catheter is located outside the skin.

The distal end 5 of the catheter is located inside the peritoneal cavity and is provided with a plurality of holes 6 along its sidewall and a tip opening 7. The catheter is shown in enlarged cross-section in FIG. 2.

In this embodiment, the outer dimater of the catheter $d_1$ is 5.0 mm and the inner diameter $d_2$ is 2.7 mm. There may be fifty-six holes with a respective spacing of 3.2 mm and with a hole diameter of about 0.7 mm positioned along the vented catheter region, which may have a length of 90 mm. The holes are approximately equal in size. These specifications may, however, vary considerably between different catheters and each manufacturer has its own construction and preferences.

FIG. 3 shows a catheter according to a preferred embodiment of the present invention. The catheter 11 is provided with a plurality of holes 16 along the wall of the catheter defining the vented catheter region 28.

The catheter may comprise an insert 18, which further comprises a restriction 19, as well as an enlarging portion 20, for example in the form of a diffusor with even cross-sectional enlargement 23 (conical), and which concludes in a tip opening 17. The inner diameter of the restriction may be 1.5 mm and the diffusor's conicity may be about 8° which, with a length of about 9 mm, results in a final opening diameter of about 2.7 mm, i.e. the same as the original inner diameter of the catheter.

The insert 18 can preferably be dimensioned so that the rate of flow or flow speed through the tip opening is approximately the same as the rate of flow through the holes in the catheter's sidewall (see discussion below for more detail).

With the aforementioned dimensions the flow through the tip opening is about 20% of the flow through the side holes, which has shown itself to be a suitable value. By means of this dimensioning, an advantage is obtained, namely that the force which the flow exerts on the catheter tip is not too large and does not cause the catheter to move to too large a degree, i.e. catheter migration is avoided. Additionally, the rate of flow through the tip opening is relatively slow, whereby the effect on the peritoneal cavity is minimised.

With certain types of catheters, it is suitable if the flow through the tip opening is less than that which is stated above, for example more than 5 or 10% of the total flow. This is particularly true for catheters with many holes in the sidewall. In certain cases, it can also be favourable if the tip opening is not present.

In other cases it may be preferable, if a larger portion of the total flow passes through the tip opening, such as up to 50% or more of the total flow. Normally, however, it is preferred that about 20% to 25% of the total flow passes through the tip opening.

The insert 18 is preferably manufactured of the same material as the rest of the catheter, such as silicon. The whole catheter is preferably made in one single piece in the same manufacturing step. Alternatively, the insert 18 can be manufactured by itself in the same material, or in another material, and it can be fastened to the catheter tip by means of welding or an adhesive, which is of course done in a biocompatible manner.

Alternatively, the insert can be manufactured of a biocompatible plastic material such as polyurethane or polycarbonate.

In a further alternative embodiment of the present invention, the insert is made of metal such as titanium or tungsten and thereby has a somewhat larger weight than if it was made of plastics material. This is favorable since the tip of the catheter will thereby automatically be orientated downwardly in the peritoneal cavity, which is generally preferred.

The insert can be embedded in a plastic material which is biocompatible. Other metals can also be used such as silver which also has a certain bacteriostatic function.

In the preferred embodiment of the present invention as shown in FIG. 3, the holes 16 are depicted as having different sizes. The object of using holes with different sizes is to obtain approximately the same rate of flow out through the various holes.

FIG. 4 shows a schematic diagram of the pressure conditions within the vented catheter region as the liquid moves toward the catheter tip. The pressure in the catheter is made up of a dynamic pressure which corresponds to the movement energy of the fluid (see curve 31) and a static pressure which constitutes the fluid's pressure against the catheter wall (see curve 32). The sum of the dynamic pressure and the static pressure corresponds to the total pressure (see curve 33). For the sake of simplicity, no account is taken of the hydrostatic pressure.

As shown by curve 31, the dynamic pressure drops towards the catheter tip which is dependent on the fact that the fluid's flow speed is reduced due to what is given out through the side holes. At the same time, the static pressure rises as shown by curve 32. The total pressure reduces slightly due to, inter alia, the frictional effect against the catheter's sidewall.

The static pressure at each side hole 16 determines the rate of flow through that hole. Thus, the side holes must have a lesser diameter nearer to the tip in order for the same rate of flow to be obtained from all the holes, whereby the frictional losses against the sidewall of the hole as well as the losses due to the fluid's viscosity reduce the outflow speed. A reduction in the outflow speed can probably be obtained in an alternative means using conical holes, where the diameter increases outwardly. Such holes can be manufactured with laser technology or in another way, such as by conical stamps.

In practice, the diameter of the holes does not have to be adapted accurately to the static pressure and it is normally sufficient if two or three different diameters are used. In FIG. 3, the holes 21 are shown with a small diameter close to the catheter tip and holes 22 with a larger diameter further away from the catheter tip.

FIG. 5 schematically shows the flow picture for a circular, relatively small hole 21 in the catheter sidewall. Along the flow lines 24 which lie closest to the sidewall, the fluid particles have a relatively low speed and can therefore, without any great difficulty, be diverted outwardly by the static pressure and pass out through the hole 21. Along flow lines 25, which are further from the sidewall the fluid particles are however more difficult to divert and do not manage to be adequately diverted before the hole 21 has been passed. The effective surface area of the hole 21 is therefore reduced. The effective surface area is dependent on the flow speed of the fluid at the hole. In order to obtain the same effective surface area, the hole's cross-sectional area therefore has to be increased further from the catheter tip.

There are thus two reasons for increasing the hole diameter as one moves farther away from the catheter tip. It is, however, not possible to increase the hole's diameter too much, as the catheter then becomes too weak and flexible.

Therefore, in accordance with the present invention, it is proposed to use oblong holes 22, such as are clearly shown in FIG. 3, for the holes which require a larger cross-sectional area. The advantage is thereby obtained that the effective surface area of the hole is better utilized than is the case with completely circular holes. Additionally, oblong holes affect the integrity of the catheter less, so that it does not become too flexible.

It can be difficult to manufacture holes with a sufficiently large surface area, despite the measures which are indicated above. It is therefore proposed in accordance with the present invention, that a restriction 26 is arranged approximately in the middle of the vented catheter region which is provided with holes, as shown in FIG. 3. However, the use of this restriction 26 is optional.

As shown schematically in FIG. 8, the restriction achieves a reduction 35 of the total pressure due to the frictional forces along the restriction, and the energy losses across the restriction, which means that the static pressure is reduced over the restriction since the dynamic pressure is unchanged before and after the restriction (the same flow speed) The static pressure before the restriction is also somewhat higher than without the restriction.

It is therefore possible to use oblong holes 22 furthest away from the tip, followed by small circular holes 21 nearer to the tip and towards the restriction 26. Downstream of the restriction oblong holes 22 are first used again and then small circular holes 21 are used closest to the tip. In this way, approximately the same flow speed is obtained through the various holes.

It can be expected that the total flow resistance for a catheter with such a restriction 26 would be greater than without a restriction. However, it has discovered that, if the restriction is placed in a certain way, the total flow resistance of the catheter may be minimized. In particular, if the restriction is placed about two thirds of the distance from the tip along the portion of the catheter provided with holes, about the same or even a lower flow resistance is obtained compared to when no restriction is present. According to the present invention, a restriction is arranged at a distance of between about 50% and 80% of the length of the vented catheter region, as measured from the tip. An explanation of this unexpected result may be that the holes prior to the restriction are used more effectively due to the increased static pressure in this portion of the catheter.

In a preferred embodiment of the present invention forty-eight holes are used, divided in the following way, as seen from the catheter tip. First there are ten circular holes with a diameter of 0.8 mm, followed by eighteen oblong holes with the dimensions 0.9 mm×2.0 mm. Then there is a restriction, followed thereafter by ten small circular holes with a diameter of 0.8 mm, followed by 10 oblong holes having the dimensions 0.9 mm×2.0 mm. The distance between the holes is 5 mm.

The restriction is dimensioned so that the flow speed through the various holes is as similar as possible. A suitable dimension is an inner diameter of 2.0 mm with a length of about 4 mm. The size is also dependent upon how the inner surface of the restriction looks, as well as on the geometry of the restriction. If the surface is rough or edged, the restriction can be shortened.

As shown in more detail in FIG. 6, the restriction 26 induces eddies 27 in the fluid flow downstream of the restriction. These eddies cause a loss of energy which reduces the total pressure, and thus also the static pressure. Moreover, energy losses arise due to frictional forces against the wall of the restriction (increased flow speed) and due to the viscosity.

The pressure conditions before and after the restriction 26 are shown schematically in FIG. 8. The curve 34 for the total pressure shows a steep drop 35 at the restriction. The curve for the dynamic pressure 36 rises sharply at the restriction, as shown by a hump 37, but returns thereafter to the same value as before the restriction, since the flow speeds are the same. The curve 38 gives the static pressure, which rises before the restriction but sinks to a lower value after the restriction, approximately corresponding to the starting value, and then rises. The two curve portions of the static pressure before and after the restriction are about the same. In this manner the two parts of the portion provided with holes are used in approximately the same way.

The aforementioned features can be combined in different ways to give the catheter desired characteristics. With catheters which are to be used for extra-sensitive patients, it may be possible to use a long portion provided with holes, which portion has many holes, and thereby use more than one restriction, such as two or three along the length of the portion having holes.

Referring to FIG. 7 it may be possible to replace the insert 18 with a restriction 42 which is relatively close to the catheter tip but also sufficiently removed from the tip opening 17 in order that the jet which is obtained from the restriction will have collected into a homogeneous flow.

The restriction 42 is positioned about 20 mm from the tip opening 17, allowing the flow to collect and reduce in speed before the flow passes through the tip opening 17.

The restrictions 26 and 42 are preferably manufactured of the same material as the rest of the catheter, such as of silicon. The whole catheter is preferably produced in one single piece and in the same manufacturing step. Alternatively, the restrictions may be inserts which are introduced into the catheter and fixed in a suitable way, such as by welding or adhesive. Alternatively, the restriction 26 can be mechanically fixed by being provided with projecting pins 43 which fit into holes 21 in the catheter's sidewall. The same materials can be used as for the insert (see above).

The length of, or the tip angle of, the conical portion 20 can be increased so that the orifice has a larger cross-section than the rest of the catheter. FIG. 6 shows an insert 48 with a larger tip angle which results in a larger outlet area and a lower outflow speed.

FIG. 7 shows further alternative embodiments of the restrictions and holes. A conical restriction 41 is thus shown which consists of a conically diminishing portion, followed by a relatively sharp edge. The fluid's flow speed increases in the conical portion, which results in a large eddy formation downstream of the sharp edge. This eddy formation brings about energy losses which result in a drop in the total pressure and the static pressure. Additionally, energy losses arise in the form of friction losses against the walls, as well as internally in the fluid due to the viscosity.

In order to avoid the effect which is shown in FIG. 5, where only a portion of the hole's effective surface area is used, it is proposed that the holes 44 and 45 are arranged at a small angle relative to the normal to the sidewall, such as 10°. Such a slanted arrangement is most noticeable at the start of the portion provided with holes where the flow speed is at its largest.

It can be difficult to reduce the static pressure sufficiently, close to the tip of the catheter. Thus, the small holes at this end can be slightly conically widened, as shown by the hole 46. Since the wall thickness is relatively small, the speed reduction will of course be correspondingly small. This hole can also be arranged in a slanted manner as shown by the hole 47.

The flow conditions for the flow of fluid into the peritoneal cavity have been described above. With outward flow, an underpressure is used which sucks the fluid out of the peritoneal cavity. For this, the proximal holes furthest from the tip are primarily used. The fluid passes to a very small extent through the tip opening and the distal holes as well as past the restriction. Only when the proximal holes become blocked due to the fluid at these holes being used up and the catheter sucking on to the peritoneal membrane, does flow occur through the distal holes. This has the beneficial effect that the restrictions do not become blocked by fibers or larger particles which may be present in the fluid in the peritoneal cavity.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A catheter adapted for insertion into a body cavity, said catheter including a proximal end, a distal end for insertion into said body cavity, and an inner flow channel, said catheter including a vented catheter region proximate to said distal end of said catheter and having a substantially constant internal diameter including a first internal diameter, a plurality of apertures, a restriction portion arranged in said vented catheter region and having a diameter less than said internal diameter, and an enlarging portion disposed between said restriction portion and said distal end of said catheter, said enlarging portion providing an expanded diameter inner flow channel, at least a portion of which having an inner diameter greater than said first internal diameter.

2. The catheter of claim 1, wherein said distal end of said catheter comprises a catheter tip including a tip opening.

3. The catheter of claim 2, wherein said portion of said catheter between said restriction portion and said tip opening is free of any of said plurality of apertures.

4. The catheter of claim 2, wherein said vented catheter region having said first internal diameter is adapted to provide for a predetermined total fluid flow therethrough, and said restriction portion and said enlarging portion are dimensioned such that the flow of said fluid through said tip opening provides between about 5% and 50% of said predetermined total fluid flow.

5. The catheter of claim 4, wherein said flow of said fluid through said tip opening comprises between about 20% and 25% of said predetermined total fluid flow.

6. The catheter of claim 2, wherein said plurality of apertures and said tip opening are dimensioned such that the rate of flow of a fluid through said plurality of apertures and through said tip opening are substantially equal.

7. The catheter of claim 2, wherein said plurality of apertures includes at least one first aperture adjacent said tip opening having a first cross-sectional area and at least one second aperture further away from said tip opening having a second cross-sectional area, said first cross-sectional area being less than said second cross-sectional area.

8. The catheter of claim 7, wherein said catheter has a longitudinal axis, and wherein said cross-sectional area of said at least one second aperture has an oval cross-section, with said longitudinal axis of said oval being substantially parallel to said longitudinal axis of said catheter.

9. The catheter of claim 1, wherein said restriction portion comprises a first restriction portion, and including a second restriction portion displaced from said first restriction portion towards said proximal end of said catheter.

10. The catheter of claim 9, wherein said portion of said catheter between said first and second restriction portions includes said plurality of apertures, and wherein the cross-sectional area of said plurality of apertures increases in the direction from said first restriction portion to said second restriction portion.

11. The catheter of claim 1, wherein said restriction portion comprises a first restriction portion, and including a second restriction portion displaced from said first restriction portion towards said proximal end of said catheter.

12. The catheter of claim 11, wherein said portion of said catheter between said first and second restriction portions includes said plurality of apertures, and wherein the cross-sectional area of said plurality of apertures increases in the direction from said first restriction portion to said second restriction portion.

13. The catheter of claim 12, wherein said enlarging portion has a diameter greater than the diameter of said restriction portion.

14. A catheter adapted for insertion into a body cavity, said catheter including a proximal end, distal end for insertion into said body cavity, and an inner flow channel, said catheter including a vented catheter region proximate to said distal end of said catheter and having a substantially constant internal diameter including a first internal diameter, a plurality of apertures, a restriction portion arranged in said vented catheter region and having a diameter less than said internal diameter, and an enlarging portion disposed between said restriction portion and said distal end of said catheter, said enlarging portion comprising a diffuser portion comprising an expanded diameter inner flow channel with a conical configuration providing an inner flow channel with a diameter greater than said diameter of said restriction portion and having a uniformly increasing diameter in the direction towards said distal end of said catheter.

15. The catheter of claim 14, wherein said enlarging portion has a diameter which successively increases in the direction towards said distal end, beginning with a diameter substantially equal to said first internal diameter.

16. The catheter of claim 14, wherein said distal end of said catheter comprises a catheter tip including a tip opening.

17. The catheter of claim 16 wherein said portion of said catheter between said restriction portion and said tip opening is free of any of said plurality of apertures.

18. The catheter of claim 16, wherein said vented catheter region having said first internal diameter is adapted to provide for a predetermined total fluid flow therethrough, and said restriction portion and said enlarging portion are dimensioned such that the flow of said fluid through said tip opening provides between about 5% and 50% of said predetermined total fluid flow.

19. The catheter of claim 18 wherein said flow of said fluid through said tip opening comprises between about 20% and 25% of said predetermined total fluid flow.

20. The catheter of claim 14 wherein said conical configuration of said inner flow channel comprises an inner wall surface having an angle with respect to a longitudinal axis of said channel of between about 1° and 10°.

21. The catheter of claim 20 wherein said inner wall surface has an angle with respect to a longitudinal axis of said channel of between about 2° and 8°.

22. The catheter of claim 21 wherein said inner wall surface has an angle with respect to a longitudinal axis of said channel of between about 4° and 5°.

23. The catheter of claim 16 wherein said plurality of apertures and said tip opening are dimensioned such that the rate of flow of a fluid through said plurality of apertures and through said tip opening are substantially equal.

24. The catheter of claim 16, wherein said plurality of apertures includes at least one first aperture adjacent said tip opening having a first cross-sectional area and at least one second aperture further away from said tip opening having a second cross-sectional area, said first cross-sectional area being less than said second cross-sectional area.

25. The catheter of claim 24 wherein said catheter has a longitudinal axis, and wherein said cross-sectional area of said at least one second aperture has an oval cross-section, with said longitudinal axis of said oval being substantially parallel to said longitudinal axis of said catheter.

26. The catheter of claim 14, wherein said restriction portion comprises a first restriction portion, and including a second restriction portion displaced from said first restriction portion towards said proximal end of said catheter.

27. The catheter of claim 26 wherein said portion of said catheter between said first and second restriction portions includes said plurality of apertures, and wherein the cross-sectional area of said plurality of apertures increases in the direction from said first restriction portion to said second restriction portion.

28. The catheter of claim 14, wherein said diameter of said enlarging portion is greater than said first internal diameter.

29. The catheter of claim 14, further including a second restriction portion arranged between the distal end and the last hole of the vented catheter region and including an enlarging portion disposed between said restriction portion and said distal end of said catheter, said enlarging portion providing an expanded diameter inner flow channel with a diameter greater than the diameter of said restriction portion.

30. The catheter of claim 29, wherein said second restriction portion is arranged at a distance of between 50% and 80% of the length of the vented catheter region as measured from the distal end.

31. The catheter of claim 29, wherein the reduced diameter portion is placed about two thirds of the distance from the distal end along the vented catheter region.

32. The catheter of claim 29, wherein several holes are arranged on each side of said restriction portion.

* * * * *

UNITED STATES PATENT AND TRADEMARK OFFICE
CERTIFICATE OF CORRECTION

PATENT NO. : 6,132,405
DATED : October 17, 2000
INVENTOR(S) : Nilsson et al.

It is certified that error appears in the above-identified patent and that said Letters Patent is hereby corrected as shown below:

<u>Title page, Item [54] and Column 1, line 1,</u>
"CATHETER FOR PERITONEAL DIALYSIS" should read -- CATHETER, IN PARTICULAR FOR PERITONEAL DIALYSIS --

<u>Column 3,</u>
Line 6, "with conical" should read -- with a conical --
Line 10, "invention the" should read -- invention, the --
Line 38, "angle of" should read -- angle with respect to a longitudinal axis of the channel --

<u>Column 4,</u>
Line 27, "diffusor" should read -- diffusor's --

<u>Column 5,</u>
Line 31, "angle ($\alpha$)" should read -- angle with respect to a longitudinal axis of the channel ($\alpha$) --

<u>Column 6,</u>
Line 52, "preferable if" should read -- preferable, if --

<u>Column 7,</u>
Line 56, "sidewall the" should read -- sidewall, the --

<u>Column 9,</u>
Line 23, "tip but" should read -- tip, but --

<u>Column 11,</u>
Line 25, "end, distal" should read -- end, a distal --

Signed and Sealed this

Fifteenth Day of April, 2003

JAMES E. ROGAN
*Director of the United States Patent and Trademark Office*